United States Patent [19]

Ohtori et al.

[11] Patent Number: 5,501,856
[45] Date of Patent: Mar. 26, 1996

[54] CONTROLLED-RELEASE PHARMACEUTICAL PREPARATION FOR INTRA-OCULAR IMPLANT

[75] Inventors: Akira Ohtori, Iizuka; Masako Andoh, Amagasaki; Yasushi Morita, Toyonaka, all of Japan

[73] Assignee: Senju Pharmaceutical Co., Ltd., Osaka, Japan

[21] Appl. No.: 799,249

[22] Filed: Nov. 27, 1991

[30] Foreign Application Priority Data

Nov. 30, 1990 [JP] Japan .................................. 2-338853

[51] Int. Cl.$^6$ .............................. A61F 2/14; A61K 47/32
[52] U.S. Cl. ...................... 424/428; 424/427; 514/772.6; 514/954; 514/955; 623/4
[58] Field of Search ..................................... 424/422, 423, 424/424, 426, 427, 428; 514/912, 913, 914, 953, 954, 955, 772.6; 623/4, 5, 901

[56] References Cited

U.S. PATENT DOCUMENTS

| | | | |
|---|---|---|---|
| 4,142,526 | 3/1979 | Zaffaroni et al. | 424/428 |
| 4,853,224 | 8/1989 | Wong | 424/427 |

Primary Examiner—Thurman K. Page
Assistant Examiner—C. Azpuru
Attorney, Agent, or Firm—Millen, White, Zelano & Branigan

[57] ABSTRACT

Presented are a controlled-release pharmaceutical preparation for intra-ocular implant to be applied to the interior of the eye after a surgical operation for disorders in retina/vitreous body or for glaucoma, which is produced by homogeneously dispersing an anti-inflammatory agent or a cell proliferation antagonist in certain polylactic acid and forming it into a particular shape; and a method for the prevention of the recurrence of said disorders or glaucoma after a surgical operation therefor.

6 Claims, No Drawings

CONTROLLED-RELEASE PHARMACEUTICAL PREPARATION FOR INTRA-OCULAR IMPLANT

BACKGROUND OF THE INVENTION

The present invention relates to a pharmaceutical preparation for implant in the field of ophthalmology, which utilizes a biodegradable polymer and has the property of gradually releasing a drug. More specifically, it relates to a controlled-release pharmaceutical preparation for intra-ocular implant to be applied after the surgical operation for disorders in retina/vitreous body or for glaucoma, which is produced by homogeneously dispersing an anti-inflammatory agent or a cell proliferation antagonist in polylactic acid, a polymer which is biodegradable, and forming the mixture into a particular shape.

Because of surgical remedies including membrane excision and silicone oil tamponade, the outcome of treatment for proliferative vitreoretinopathy has been markedly improved. However, recurrence has been reported in many cases in 4 to 6 weeks after the operation where only a surgical treatment was conducted (Machemer, R. et al., Ophthalmology, 85, 584–593 (1978)). Therefore, a variety of experimental attempts have been made concerning nedical therapy for the prevention of recurrence after operation.

Thus, for example, intra-vitreous injection of steroids, 5-fluorouracil and the like has been found effective on proliferative vitreoretinopathy (Tano, Y. et al., An. J. Ophthalmol., 89, 131–136 (1980) and Blumenkranz, M. S. et al., An. J. Ophthalnol. 94, 458–467 (1982)), and it has also been reported that the effect of filtering operation for glaucoma can be maintained by controlling the healing of intraocular tissues by subconjunctival injection of 5-fluorouracil, which is conducted once a day during the 1st week and once every other day during the 2nd week after the operation, so as to allow the drug to be transported into the eyeball (Nakano et al., Rinsho Ganka, 43, 1929–1933 (1989)).

However, it has been known that the intravitreous simple injection of drugs such as steroids and 5-fluorouracil involves a risk of cause damage to intra-ocular tissues, depending upon the dose applied, due to the exposure of intra-ocular tissues to the highly concentrated drugs at a tine (Shinada et al, Acta Soc. Ophthalmol. Jpn., 93, 501–510 (1989)). Moreover, repeated subconjunctival injections after glaucoma operation will impose excessive pain, physical as well as psychological, on the patient.

In order to solve these problems, studies have been conducted, for example, about a certain form of pharmaceutical preparation in which a drug is contained in microsphere particles so as to keep, for a particular period of time, the intraocular concentration of the drug at the level required to manifest its effect (Moridera et al., Acta Soc. Ophthalmol. Jpn., 94, 508–513 (1990)). Moreover, steroids in suspension forms are also expected to have a similar effect.

However, when these pharmaceutical preparations are injected intra-ocularly, for example into the vitreous body, there is involved a high risk that the microsphere particles and suspension particles will, as foreign matters, contact with and be accumulated on the surface of tissues such as the lens capsule and the corneal endothelium or that the drugs eluted therefrom will be accumulated at a high level in the lens and the cornea, thereby causing severe side-effects such as opacification of these transparent tissues. Thus, their safety has not yet been established.

In such circumstances, there has been a great need for a safe pharmaceutical preparation form which will release drugs Gradually and continuously so as to make it possible to maintain the intra-ocular concentration of the drugs at a therapeutic level for a desired period of time after an intra-ocular single administration.

With this background, the inventors conducted an intensive study to develop a controlled-release pharmaceutical preparation for intra-ocular use. As a result, the inventors have found that these requirements are fulfilled by a pharmaceutical preparation for intra-ocular implant which is produced by homogeneously dispersing a drug in a biodegradable polylactic acid with a particular range of Mn (number-average molecular weight), and forming the mixture into a desired shape. Through the accumulation of further studies, the present invention has been accomplished.

SUMMARY OF THE INVENTION

Therefore, the present invention relates to a controlled-release pharmaceutical preparation for intra-ocular implant consisting of an anti-inflammatory agent or a cell proliferation antagonist and polylactic acid, a biodegradable polymer which is characterized in that either a polylactic acid having an Mn of about 2000–about 4000, preferably about 2500–about 3500, most preferably about 3200, or a polylactic acid having an Mn of about 5000–about 7000, preferably about 5500–about 6500, most preferably about 5900, or a mixture of the both polylactic acids at a particular weight ratio is used, thereby enabling the intra-ocular release of the drug for a certain desired period of time.

DETAILED DISCUSSION

The drugs which may be employed in the controlled-release pharmaceutical preparation for intra-ocular implant of the present invention are anti-inflammatory agents and cell proliferation antagonists, which may include, for example, steroids such as dexamethasone m-sulfobenzoate sodium salt, hydrocortisone acetate, fluorometholone and the like, and pyrimidine metabolism antagonists such as 5-fluorouracil and the like.

The biodegradable polymers which may be used in the controlled-release pharmaceutical preparation for intra-ocular implant of the present invention are polylactic acid having an Mn of about 2000–about 4000, preferably about 2500–about 3500, most preferably about 3200, and polylactic acids having an Mn of about 5000–about 7000, preferably about 5500–about 6500, most preferably about 5900, which may be used solely or in the form of a mixtures thereof at a weight ratio, for example, in the range from 10 parts/90 parts to 90 parts/10 parts, and preferably in the range from 30 parts/70 parts to 70 parts/30 parts, depending upon the desired period of time for the controlled release of the drugs.

The controlled-release pharmaceutical preparation for intra-ocular implant of the present invention is a pharmaceutical preparation with a particular shape consisting of a homogeneous mixture of a drug and polylactic acid, wherein the content of the drug is 10 to 70% by weight, preferably 40 to 60% by weight, based on the total weight of the preparation.

The controlled-release pharmaceutical preparation for intra-ocular implant of the present invention may be short stick-shaped, needle-shaped or film-shaped, and it may be produced by general forming methods, including molding method with the aid of a solvent, melting method, pressure method or pressure heat melting method.

According to the controlled-release pharmaceutical preparation for intra-ocular implant of the present invention, drugs may be applied gradually and continuously to intra-ocular tissues for a long period of time. Furthermore, as shown in Test example 1, the rate of drug release may be easily controlled by modifying the mixing ratio of the two types of polylactic acids which differ in Mn. Thus, it is also possible to design the pharmaceutical preparation so that the drug may be continuously released over a shorter or much longer period of time as desired, for example, 2 weeks or 8 weeks.

Therefore, according to the present invention, there may be provided a very useful controlled-release pharmaceutical preparation for prevention of recurrence after a corrective surgical operation for proliferative vitreoretinopathy or glaucoma, wherein the composition has a variety of advantages, i.e., (1) it is free of a risk of causing severe side effects on ocular tissues such as the lens and the cornea, (2) it will not impose excessive pain on the patient, which might be caused by repeated subconjunctival injections, (3) it may allow the drug to exhibit the full effect since the suitable length of time for continuous release of the drug may be set according to the condition of the disorder, and (4) that it will by no means cause problems due to residues since a non-toxic biodegradable polymer is used.

The present invention will be explained in further detail according to the examples below.

EXAMPLE 1

A controlled-release pharmaceutical preparation for intra-ocular implant containing dexamethasone m-sulfobenzoate sodium salt Dexamethasone m-sulforbenzoate sodium salt and polylactic acid were admixed mechanically so as to attain each ratio of constituents as shown in Table 1 below, charged in a Teflon tube having an inner diameter of 0.8 mm, and then pressed through both ends with stainless steel rods while heating to about 80° C. to form a short stick having a diameter of 0.8 mm and a length of 5 mm.

Dexamethasone m-sulfobenzoate sodium salt and polylactic acid were admixed so as to attain each ratio of constituents as shown in Table 1 below, and dissolved in 50 ml of a mixture solution of methanol/acetonitrile (4/1). The mixture was poured to spread in a Teflon container and dried at room temperature to form a sheet. Then the sheet thus formed was rolled to form a film having a thickness of about 600 μm.

TABLE 1

| Sample No. | Dexamethasone m-sulfobenzoate sodium salt | Polylactic acid (Mn = 3200) | Polylactic acid (Mn = 5900) |
|---|---|---|---|
| 1 | 0.1 g | 0.1 g | — |
| 2 | 0.1 g | 0.07g | 0.03g |
| 3 | 0.1 g | 0.05g | 0.05g |
| 4 | 0.1 g | 0.03g | 0.07g |
| 5 | 0.1 g | — | 0.1 g |

Mn; number-average molecular weight

EXAMPLE 2

A controlled-release pharmaceutical preparation for intra-ocular implant containing hydrocortisone acetate 0.1 g of hydrocortisone acetate and 0.1 g of the polylactic acid having an Mn of 3200 were admixed mechanically, charged in a Teflon tube having an inner diameter of 0.8 mm, and then pressed through both ends with stainless steel rods while heating to about 80° C. to form a short stick having a diameter of 0.8 mm and a length of 5 mm.

EXAMPLE 3

A controlled-release pharmaceutical preparation for intra-ocular implant containing fluorometholone 0.1 g of fluorometholone and 0.1 g of the polylactic acid having an Mn of 3200 were admixed mechanically, charged in a Teflon tube having an inner diameter of 0.8 mm, and then pressed through both ends with stainless steel rods while heating to about 80° C. to form a short stick having a diameter of 0.8 mm and a length of 5 min.,

EXAMPLE 4

A controlled-release pharmaceutical preparation for intra-ocular implant containing 5-fluorouracil 0.1 g of 5-fluorouracil and 0.1 g of the polylactic acid having an Mn of 5900 were admixed mechanically, charged in a Teflon tube having an inner diameter of 0.8 mm, and then pressed through both ends with stainless steel rods while heating to about 80° C. to form a short stick having a diameter of 0.8 mm and a length of 5 mm.

Test example 1

Test of the releasing property of the preparations produced in Example 1

The short stick-shaped pharmaceutical preparations containing dexamethasone m-sulfobenzoate sodium salt produced in Example 1 was soaked in 100 ml of a pH 7.4 buffer solution shown below and agitated at 37° C. to evaluate their drug releasing property.

| | |
|---|---|
| Sodium chloride | 0.7959 g |
| Potassium chloride | 0.036 g |
| Calcium chloride | 0.018 g |
| Sodium citrate | 0.1 g |
| Sodium acetate | 0.06 g |
| Sterile purified water | 100 ml |

As a result, it was demonstrated that the remaining content of dexamethasone m-sulfobenzoate sodium salt in the preparations 4 weeks after the start of the test was 50 % in sample No. 1 and 83% in sample No. 5, compared with the initial content.

Then, each of the short stick-shaped pharmaceutical preparations produced in Example 1 was inserted in the vitreous body of a rabbit to evaluate the drug releasing property. As a result, it was demonstrated that the content of dexamethasone m-sulfobenzoate sodium salt remaining in the preparations 4 weeks after the start of the test was 0%, 13%, 15%, 50% and 82% of initial content in samples Nos. 1, 2, 3, 4 and 5, respectively.

These results indicate that present invention permits application of drugs to the interia of the eye continuously for a very long period of time. Moreover, the higher the ratio of the polylactic acid having an Mn of 5900 is, the slower the rate of drug release becomes. Therefore, the rate of release of the drug may be varied by altering the ratio of the contained polylactic acids having an Mn of 3200 and 5900, respectively.

Therefore, by adjusting the ratio of each polylactic acid content to the whole amount of polylactic acid within the range from 0% to 100% while taking into consideration the inherent solubility of the applied drug to water, it is possible to easily attain the continuous application of the drug to intra-ocular tissues for a desired period of time ranging from a short period to a much longer period, according to the purpose of the treatment and the severity of the disorder.

Test example 2

Test of the releasing property of the preparation produced in Example 2

The short stick-shaped pharmaceutical preparation containing hydrocortisone acetate produced in Example 2 was inserted in the vitreous body of a rabbit to evaluate the drug releasing property. As a result, it was determined that the content of hydrocortisone acetate remaining in the preparation 4 weeks after the start of the test was 20% of the initial content.

Test example 3

Test of the releasing property of the preparation produced in Example 3

The short stick-shaped pharmaceutical preparation containing fluorometholone produced in Example 3 was evaluated analogously to Test example 2. As a result, the remaining content of the drug in the preparation 4 weeks after the start of the test was 56% of the initial content.

What is claimed is:

1. A method for the prevention of the recurrence of proliferative vitreoretinopathy or of glaucoma after a surgical operation for the treatment thereof comprising placing in the interior of the operated eye a controlled-release pharmaceutical preparation in the shape of a stick, needle or film adapted for introduction into the vitreous cavity as an intraocular implant and produced by (a) homogeneously dispersing as an active agent therein at least one anti-inflammatory steroid or one cell proliferation antagonist in a polylactic acid with a number-average molecular weight of about 2,000 to about 4,000 or with a number-average molecular weight of about 5,000 to about 7,000, or a mixture thereof, and (b) forming the dispersion of anti-inflammatory steroid or one cell proliferation antagonist in the polylactic acid into the shape of a stick, needle or film adapted for introduction into the vitreous cavity as an intra-ocular implant.

2. The method of claim 1, wherein said anti-inflammatory steroid is dexamethasone m-sulfobenzoate sodium salt, hydrocortisone acetate or fluoromethalone.

3. The method of claim 1, wherein said cell proliferation antagonist is a pyrimidine metabolism antagonist.

4. The method of claim 3, wherein said pyrimidine metabolism antagonist is 5-fluorouracil.

5. A method according to claim 1, wherein the pharmaceutical preparation is in the form of a film.

6. A method according to claim 1, wherein the pharmaceutical preparation is in the form of a short stick.

* * * * *